United States Patent
Anderle et al.

(10) Patent No.: US 11,441,554 B2
(45) Date of Patent: Sep. 13, 2022

(54) OPERATING DEVICE, METHOD FOR OPERATING AN OPERATING DEVICE, DIAPHRAGM PUMP HAVING AN OPERATING DEVICE AND A DIAPHRAGM PUMP DEVICE, AND A BLOOD TREATMENT APPARATUS HAVING A DIAPHRAGM PUMP

(71) Applicant: FRESENIUS MEDICAL CARE DEUTSCHLAND GMBH, Bad Homburg (DE)

(72) Inventors: Jens Anderle, Deggingen (DE); Hannes Wirtl, Schongau (DE)

(73) Assignee: FRESENIUS MEDICAL CARE DEUTSCHLAND GMBH, Bad Homburg (DE)

( * ) Notice: Subject to any disclaimer, the term of this patent is extended or adjusted under 35 U.S.C. 154(b) by 241 days.

(21) Appl. No.: 16/470,564

(22) PCT Filed: Dec. 18, 2017

(86) PCT No.: PCT/EP2017/083404
§ 371 (c)(1),
(2) Date: Jun. 18, 2019

(87) PCT Pub. No.: WO2018/114862
PCT Pub. Date: Jun. 28, 2018

(65) Prior Publication Data
US 2019/0353159 A1 Nov. 21, 2019

(30) Foreign Application Priority Data
Dec. 21, 2016 (DE) ...................... 10 2016 015 207.9

(51) Int. Cl.
*F04B 43/073* (2006.01)
*F04B 49/22* (2006.01)
(Continued)

(52) U.S. Cl.
CPC ......... *F04B 43/073* (2013.01); *A61M 60/268* (2021.01); *F04B 43/06* (2013.01);
(Continued)

(58) Field of Classification Search
CPC ...... F04B 9/12–1207; F04B 9/123–125; F04B 43/06; F04B 43/073; F04B 43/0733;
(Continued)

(56) References Cited

U.S. PATENT DOCUMENTS 2,383,193 A * 8/1945 Herbert ................ F04B 7/0275
417/317
3,154,021 A * 10/1964 Vick, Jr. ............. F04B 43/1133
417/394
(Continued)

FOREIGN PATENT DOCUMENTS

DE     2118056 A1    11/1971
DE     10216146 A1   10/2003
(Continued)

OTHER PUBLICATIONS

International Search Report and Written Opinion issued in corresponding International Patent Application No. PCT/EP2017/083404 (with English translation of International Search Report) dated Feb. 28, 2018 (13 pages).

(Continued)

*Primary Examiner* — Alexander B Comley
(74) *Attorney, Agent, or Firm* — Kilyk & Bowersox, P.L.L.C.

(57) ABSTRACT

An actuating device mechanically controls a membrane pump device. The device includes a base body having a mounting face for a membrane pump device and through which a control fluid line passes that extends from a control fluid port to a control fluid opening that opens at the mounting face. A control fluid valve arranged in the control (Continued)

Figure 1:
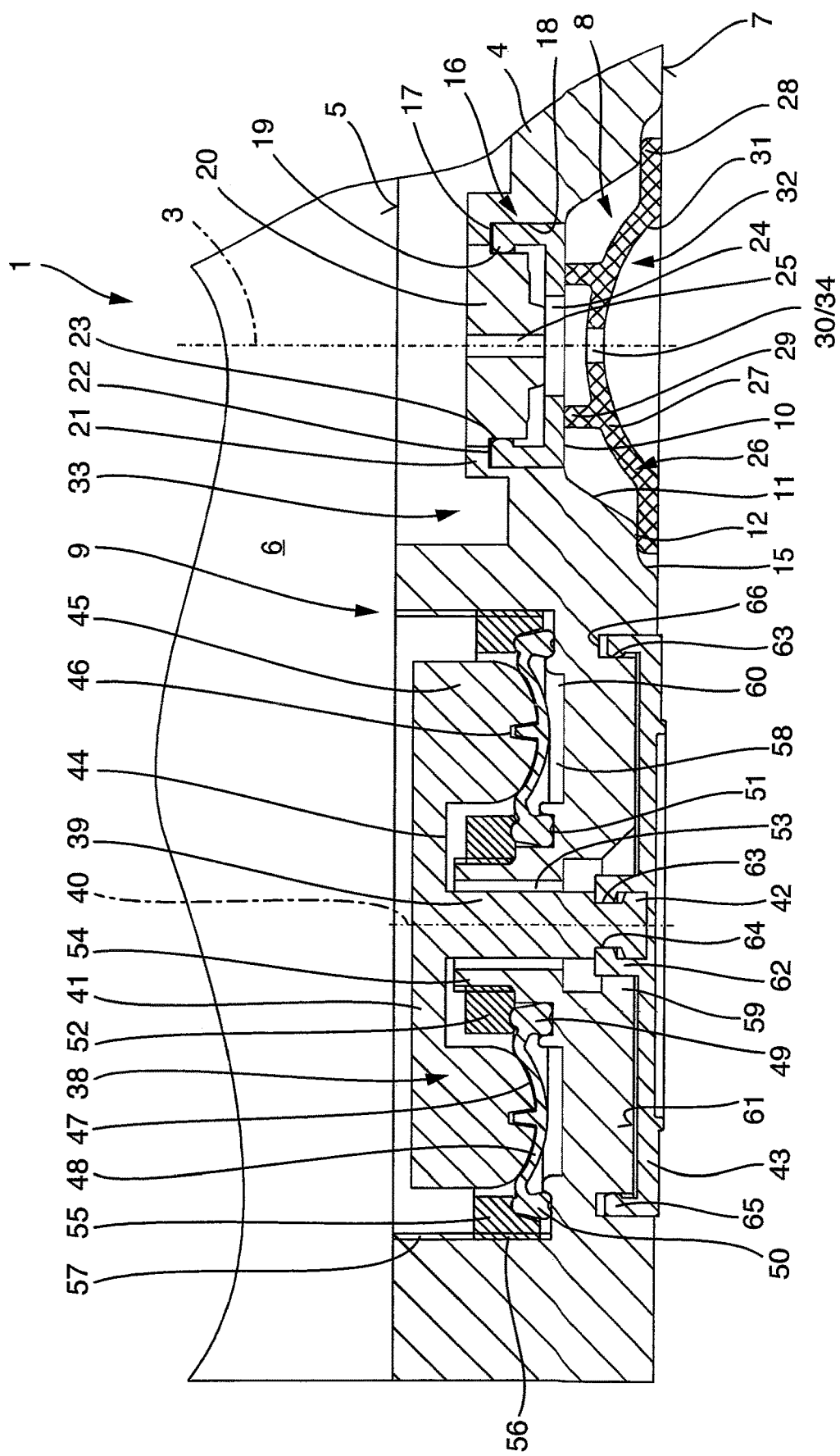

fluid line influences a cross-section of the control fluid line and has an adjustment device that has a fluid actuator arranged on the mounting face. A working fluid valve influences a cross-section of a working fluid line that passes through the base body. The control fluid valve and the working fluid valve are electrically connected to a control device that electrically controls the control fluid valve and the working fluid valve. Moreover, a membrane pump is provided that has an actuating device and a membrane pump device.

17 Claims, 4 Drawing Sheets

(51) Int. Cl.
    *F04B 43/06*     (2006.01)
    *F04B 49/06*     (2006.01)
    *A61M 60/268*     (2021.01)

(52) U.S. Cl.
    CPC ........ *F04B 43/0733* (2013.01); *F04B 49/065* (2013.01); *F04B 49/22* (2013.01); *F04B 2201/12* (2013.01); *F04B 2205/01* (2013.01)

(58) Field of Classification Search
    CPC .... F04B 49/065; F04B 49/22; F04B 2201/12; F04B 2205/01; F04B 43/065; A61M 60/268
    USPC .......................................... 417/394, 395, 507
    See application file for complete search history.

(56) References Cited

U.S. PATENT DOCUMENTS

| | | | | |
|---|---|---|---|---|
| 3,357,360 A * | 12/1967 | Borell | ............. | F04B 43/073 417/390 |
| 3,689,204 A * | 9/1972 | Prisk | ............. | F04B 43/025 417/394 |
| 3,741,687 A * | 6/1973 | Nystroem | ............. | F04B 7/0275 417/317 |
| 4,158,530 A * | 6/1979 | Bernstein | ............. | F04B 43/1133 417/389 |
| 4,290,346 A * | 9/1981 | Bujan | ............. | F04B 43/0054 417/478 |
| 4,479,762 A * | 10/1984 | Bilstad | ............. | A61M 1/306 417/395 |
| 4,583,920 A * | 4/1986 | Lindner | ............. | F04B 43/0733 417/266 |
| 4,646,781 A * | 3/1987 | McIntyre | ............. | A61M 39/24 137/512.4 |
| 5,076,890 A * | 12/1991 | Balembois | ............. | G05D 7/0635 162/198 |
| 5,088,515 A * | 2/1992 | Kamen | ............. | F16K 31/005 137/15.17 |
| 5,195,986 A * | 3/1993 | Kamen | ............. | A61M 5/162 604/251 |
| 5,252,041 A * | 10/1993 | Schumack | ............. | F04B 43/073 417/395 |
| 5,499,909 A * | 3/1996 | Yamada | ............. | F04B 43/043 417/384 |
| 5,593,290 A * | 1/1997 | Greisch | ............. | F04B 43/021 417/478 |
| 5,725,363 A * | 3/1998 | Bustgens | ............. | F04B 43/043 417/413.1 |
| 6,033,191 A * | 3/2000 | Kamper | ............. | F04B 43/043 417/322 |
| 6,223,130 B1 * | 4/2001 | Gray | ............. | F04B 43/009 700/282 |
| 6,520,753 B1 * | 2/2003 | Grosjean | ............. | F04B 19/24 417/379 |
| 7,284,966 B2 * | 10/2007 | Xu | ............. | F04B 53/106 417/395 |
| 7,763,453 B2 * | 7/2010 | Clemmens | ............. | B01F 13/0059 435/286.7 |
| 7,832,429 B2 * | 11/2010 | Young | ............. | F16K 99/0055 137/829 |
| 8,197,231 B2 * | 6/2012 | Orr | ............. | A61M 1/3666 417/395 |
| 8,292,594 B2 * | 10/2012 | Tracey | ............. | F04B 23/06 417/43 |
| 8,323,586 B2 * | 12/2012 | Zhou | ............. | B01L 3/502715 422/502 |
| 2003/0194328 A1 | 10/2003 | Bryant et al. | | |
| 2003/0194332 A1 * | 10/2003 | Jahn | ............. | F04B 43/0733 417/395 |
| 2004/0019313 A1 * | 1/2004 | Childers | ............. | A61M 1/28 604/5.01 |
| 2007/0077156 A1 * | 4/2007 | Orr | ............. | F04B 7/02 417/395 |
| 2008/0202591 A1 * | 8/2008 | Grant | ............. | F04B 23/06 137/12 |
| 2009/0137940 A1 * | 5/2009 | Orr | ............. | A61M 60/148 604/6.11 |
| 2013/0032210 A1 * | 2/2013 | Johnstone | ............. | F04B 19/006 137/1 |
| 2013/0058805 A1 * | 3/2013 | Chien | ............. | F04B 43/1133 417/395 |
| 2013/0178752 A1 * | 7/2013 | Kodama | ............. | F16K 15/145 600/498 |
| 2014/0251450 A1 | 9/2014 | Hettinger et al. | | |
| 2016/0118573 A1 * | 4/2016 | Palermo | ............. | H01L 41/094 251/129.06 |

FOREIGN PATENT DOCUMENTS

DE       102013102397 A1     9/2014
EP             1353069 A2     10/2003

OTHER PUBLICATIONS

International Preliminary Report on Patentability issued in corresponding International Patent Application No. PCT/EP2017/083404 dated Jun. 25, 2019 (7 pages).

\* cited by examiner

OPERATING DEVICE, METHOD FOR OPERATING AN OPERATING DEVICE, DIAPHRAGM PUMP HAVING AN OPERATING DEVICE AND A DIAPHRAGM PUMP DEVICE, AND A BLOOD TREATMENT APPARATUS HAVING A DIAPHRAGM PUMP

This application is a National Stage Application of PCT/EP2017/083404, filed Dec. 18, 2017, which claims priority to German Patent Application No. 10 2016 015 207.9, filed Dec. 21, 2016.

The invention relates to an actuating device for mechanically controlling a membrane pump device, and to a method for operating such an actuating device. The invention relates additionally to a membrane pump which has such an actuating device and such a membrane pump device, as well as to a blood treatment device, in particular a dialysis device, which has such a membrane pump.

Membrane pumps are used in medical technology for conveying medical liquids. The advantage of membrane pumps is that the drive unit is separated from the fluid to be conveyed by a membrane.

In medical technology, high demands are made of membrane pumps. For certain applications, the membrane pumps are to have high conveying accuracy even at low flow rates. Citrate anticoagulation (CiCa anticoagulation) in dialysis, for example, requires particularly accurate metering at a low flow rate.

Membrane pumps are known which have a membrane pump device that is intended only for single use. The membrane pump device of these membrane pumps can be in the form of a disposable cassette in which there is formed a recess closed by a resilient membrane. During the suction phase, the flow of fluid from the pump chamber is interrupted, and during the pressure phase, the flow of fluid into the pump chamber is interrupted. The resilient membrane can be driven by an actuating device which is not intended for single use.

An actuating device of the generic type is used to mechanically control a membrane pump device in order to convey a fluid, which in particular can be a liquid, from an input port of the membrane pump device to an output port of the membrane pump device. The membrane pump device comprises, by way of example, a planar channel body on which a suction channel extends from an input port to a pump chamber, and on which a pressure channel extends from the pump chamber to an output port. It is provided for the pump chamber to be introduced in the form of a recess into a surface of the channel body and to be closed by a membrane that is attached to the channel body in a sealing manner. By moving the membrane, a volume of the pump chamber is changed so that, provided in addition that the suction channel and the pressure channel are blocked and released cyclically, a mass flow rate for the fluid can be generated.

The object of the invention is to produce an actuating device for controlling a membrane pump device which allows a conveying operation of a membrane pump device to be carried out reliably, and to provide a method for operating an actuating device which allows a conveying operation of a membrane pump device to be carried out reliably.

A further object of the invention is to improve the conveying accuracy of a membrane pump for conveying a medical liquid, in particular to produce a membrane pump which allows particularly accurate metering of fluids, for example of a solution for CiCa anticoagulation, even at very low flow rates, it being the intention to ensure a constant mass flow rate of fluid.

Moreover, the invention addresses the problem of providing a blood treatment device, in particular a dialysis device, having a membrane pump which allows particularly accurate metering of a fluid, for example a solution for CiCa anticoagulation, even at very low flow rates having a constant mass flow rate of fluid.

The objects are achieved according to the invention by the features of the independent patent claims. The dependent claims relate to advantageous embodiments of the invention.

The actuating device according to the invention has a base body which comprises a mounting face for a membrane pump device and through which a control fluid line passes which extends from a control fluid port to a control fluid opening which opens at the mounting face, a control fluid valve being arranged in the control fluid line and being designed to influence a cross section of the control fluid line. The actuating device further comprises an adjustment device, which has a fluid actuator arranged on the mounting face for providing an adjustment movement, and a working fluid valve which is designed to influence a cross section of a working fluid line which passes through the base body, and the control fluid valve and the working fluid valve being electrically connected to a control device which is designed to electrically control the control fluid valve and the working fluid valve.

The base body can be either in one piece or in multi-part form and is equipped at least with an interface, referred to as the mounting face, for the coupling of a membrane pump device. Depending on the design of the membrane pump device, the mounting face can be planar or in the form of a three-dimensionally structured face, in particular having flat regions. In order to allow actuation of the membrane pump device, which in particular is in the form of a wholly passive structural element without its own actuator system and/or sensor system, a control fluid line passes through the base body and extends from a control fluid port to a control fluid opening. The control fluid port can be arranged directly on the base body or it can be spaced apart from the base body, it being possible in this case for a hose connection, for example, to be provided between the control fluid port and the control fluid line. The control fluid line extends, starting from the control fluid port, to the control fluid opening, which opens at the mounting face. For example, a control fluid source, in particular a compressed air source, or a control fluid sink, in particular a vacuum generator, can be connected to the control fluid port. By means of the control fluid, a movement of a pump membrane of the membrane pump device is generated by cyclic or acyclic pressurisation and/or vacuum application, so that a fluid to be conveyed can be drawn into a pump chamber and/or ejected/discharged from the pump chamber by the pump membrane. In order to be able to influence a flow of control fluid, a control fluid valve is arranged in the control fluid line, which control fluid valve is designed to influence a cross section of the control fluid line, in particular between a closed position for complete blocking of the control fluid line and an open position for complete release of the cross section of the control fluid line.

Also associated with the base body is an adjustment device which is designed to mechanically actuate a membrane valve provided on the membrane pump device. This membrane valve can be fluidically connected, for example, to the pump chamber, which is likewise formed in the membrane pump device, and can be configured to control a flow of fluid into the pump chamber or out of the pump chamber. For actuation of the membrane valve, the adjustment device has a fluid actuator arranged on the mounting face, which fluid actuator is, by way of example, a pneumatic cylinder of compact construction. The adjustment device comprises a movable actuator member which can be moved in a linear and/or rotatory manner between a rest position and a functional position and protrudes beyond the mounting face in particular in the functional position. As a result, a membrane of the membrane valve of the membrane pump device which can be attached opposite can be locally deformed in order, for example, to bring about a closed position of the membrane valve. It can further be provided that the membrane valve is in an open position when the actuator member assumes the rest position, which in particular is flush with the surface of the mounting face. For fluidic control of the fluid actuator of the adjustment device a working fluid valve is provided which is associated with a working fluid line which passes through the base body. The working fluid valve can thereby be switched or adjusted, by way of example, between a closed position for complete blocking of the working fluid line and an open position for complete release of the cross section of the working fluid line. The working fluid for actuating the fluid actuator can be provided, by way of example, via a separate working fluid port to which a fluid source or a fluid sink for providing a pressurised working fluid or a vacuum can be connected. Alternatively, the working fluid line can be connected to the control fluid port.

Both the control fluid valve and the working fluid valve are electrically connected to a control device which is designed to electrically control the control fluid valve and the working fluid valve. By way of example, the control device can be a microprocessor or microcontroller which are designed to execute a predefinable control program for the control fluid valve and the working fluid valve. The control device can in turn be provided for communication with a higher-order control arrangement, in particular a programmable logic controller, and can comprise for that purpose a suitable communication interface, in particular a multipole interface or a bus interface.

A preferred embodiment of the invention provides for a control fluid pressure sensor to be arranged on the base body, which control fluid pressure sensor is electrically connected to the control device and is designed to detect a control fluid pressure. The control fluid pressure sensor can be fluidically connected to the control fluid line via a fluid line or it can be arranged in the control fluid line or arranged adjacent to the control fluid opening and serves to detect the control fluid pressure which can be applied to the pump membrane when the actuating device is coupled to a membrane pump device. On the basis of the measured control fluid pressure and/or a time derivative of the measured control fluid pressure, conclusions can be drawn in the control device regarding the manner in which the pump membrane is deformed and a conveying operation for the fluid to be conveyed by means of the membrane pump device is performed.

In a further development of the invention it is provided for a working fluid pressure sensor to be arranged in the working fluid line, which working fluid pressure sensor is electrically connected to the control device and designed to detect a working fluid pressure. The working fluid pressure sensor can be fluidically connected to the working fluid line via a sensor line or it can be arranged in the working fluid line. A sensor signal of the working fluid pressure sensor is processed either in the working fluid valve and/or in the control device and serves in particular to regulate the working fluid pressure which is provided at the fluid actuator. When the sensor signal of the working fluid pressure sensor is provided to the control device, the fluid actuator, which by way of example is designed to actuate a membrane valve of the membrane pump device, can be controlled particularly precisely by additionally including the sensor signal of the control fluid pressure sensor.

In a further embodiment of the invention it is provided for a concave control chamber to be formed on the mounting face as a movement chamber for a pump membrane, and for the control fluid opening to open at a surface of the control chamber. The concave control chamber allows an advantageous pump stroke for the membrane pump formed on the membrane pump device, since, in addition to a concave deformation state which is possible in any case when the control fluid line is pressurised, the membrane of the membrane pump can also be brought into a convex deformation state, which can occur when a vacuum is applied to the control chamber. In the control chamber, a fluid-permeable moulded body is preferably provided which is spaced apart from the surface of the control chamber and which, when a vacuum is applied to the membrane of the membrane pump, serves as a contact face for the membrane. A spatial volume between the surface of the control chamber and a contact face of the shaped body facing the membrane serves as a working chamber for the control fluid which can be made available at the control fluid opening and which, for example after a vacuum has been applied to the control chamber and the membrane as a result rests flat on the contact face, is to be used for a discharge operation of the membrane pump.

In the base body, a vacuum line is preferably formed which extends from a vacuum port to the control chamber or to the control fluid line and in which vacuum line a vacuum valve is arranged which is designed to influence a cross section of the vacuum line, the vacuum valve being electrically connected to the control device. Depending on the form of the control chamber and of the moulded body optionally accommodated therein, it can be provided for the vacuum line either to open directly at the surface of the control chamber or to be fluidically connected to the control fluid line. By acting in a cyclical alternating manner on the control chamber and the membrane of the membrane pump device which can be coupled thereto, a pump movement for the membrane between a concave deformation state when the control fluid line is pressurised and a convex deformation state, and thus a maximum pump stroke, is made possible. The vacuum line is likewise a control fluid line.

It is advantageous if the working fluid line is fluidically connected to the control fluid port.

In an advantageous further development of the invention it is provided for the control device to include an observer algorithm which is designed to determine a mass flow rate of fluid in a membrane pump device on the basis of the pressure signal of the control fluid pressure sensor. The purpose of the observer algorithm is to determine the mass flow rate of fluid in the membrane pump device without a sensor device for that purpose being directly integrated in the membrane pump device. The observer algorithm can be in the form of a system of equations or in the form of a neural network, for example. The observer algorithm is preferably calibrated by means of a reference arrangement which comprises the actuating device and the membrane pump device attached thereto as well as an external, accurate flow meter, by comparing the signals of the control fluid pressure sensor and the external flow meter.

In a particularly preferred embodiment, a first adjustment device having a first working fluid valve and a second adjustment device having a second working fluid valve are arranged on the base body, the first working fluid valve being in the form of a switch valve and the second working fluid valve being in the form of a proportional valve, in particular in the form of a pressure regulating valve. As a result, the actuating device, when the membrane pump device is coupled thereto, can both influence a fluid inflow into the pump chamber and influence a fluid outflow from the pump chamber. The control device is preferably designed such that it allows cyclically recurring opposite control of the two adjustment devices depending on the provision of control fluid to the control chamber. It is preferably provided for the first adjustment device to be operated in a controlled operation, while the second adjustment device is operated in a regulated operation, in particular depending on a sensor signal of a working fluid pressure sensor associated with the second working fluid valve. In regulated operation, the second working fluid valve acts as a pressure regulating valve. It can thereby be ensured in particular that a narrow limited flow interval for a mass flow rate of fluid which is conveyed by the membrane pump device during a pump stroke is maintained.

In the method according to the invention for operating an actuating device, the working fluid valve is controlled by the control device which, using an observer algorithm, determines a mass flow rate of fluid in a membrane pump device on the basis of the pressure signals of a control fluid pressure sensor and which determines a target pressure value for the working fluid valve depending on the determined mass flow rate of fluid, in order to ensure a constant mass flow rate of fluid during a discharge phase of the membrane pump device.

In a further development of the method it is provided for the control device to control the control fluid valve and the vacuum valve during a discharge phase of the membrane pump device in such a manner that the control fluid line and the vacuum line are blocked. Accordingly, the discharge of the fluid from the pump chamber of the membrane pump takes place without a further inflow of control fluid into the control chamber but instead on the basis of the control fluid pressure present in the control chamber at the beginning of the discharge phase, in conjunction with the internal stress in the deformed membrane of the membrane pump. The control fluid pressure can accordingly be used as a measure of the change in volume in the control chamber and thus indirectly as a measure of the mass flow rate of fluid from the pump chamber of the membrane pump.

The membrane pump device according to the invention, which can be mechanically controlled by the actuating device according to the invention, preferably has a pump chamber body in which there is formed a recess which is closed by a resilient membrane to form a pump chamber. In addition, the membrane pump device comprises an inflow path, which connects an input port to an inlet opening of the pump chamber, and an outflow path, which connects an outlet opening of the pump chamber to an output port. An inlet valve is provided in the inflow path and an outlet valve is provided in the outflow path, in order to be able to influence the flow of liquid in the inflow or outflow path.

The membrane pump device, or a portion of the membrane pump device, can be in the form of a cassette intended for single use, which is intended to be used with the actuating device of the membrane pump. The membrane pump device can be in the form of a device which can be coupled to a mounting face of the actuating device. The membrane pump device and the actuating device can, however, also be devices which are not separable from one another in use.

The membrane pump according to the invention comprises the actuating device according to the invention and the pump device according to the invention.

The membrane pump can advantageously be used in medical technology. However, there are also advantages when it is used in other fields of technology. A particularly preferred use is the use of the membrane pump in a blood treatment device, in particular a dialysis device, having a container for providing a medical liquid, in particular an anticoagulation solution, which is to be conveyed with particularly high conveying accuracy at a relatively low flow rate.

An embodiment of a membrane pump which comprises a pump device and an actuating device is described in detail below.

Figure 2:
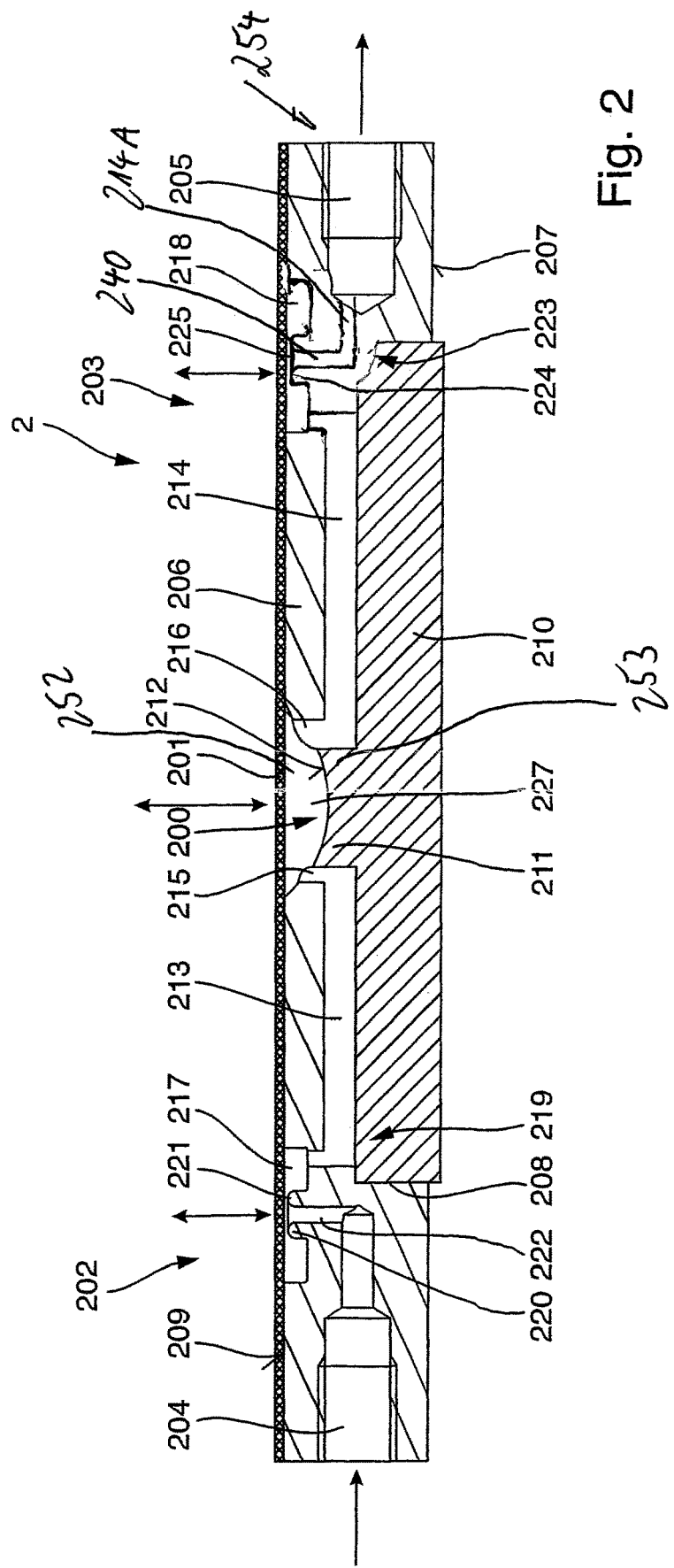
Figure 3:
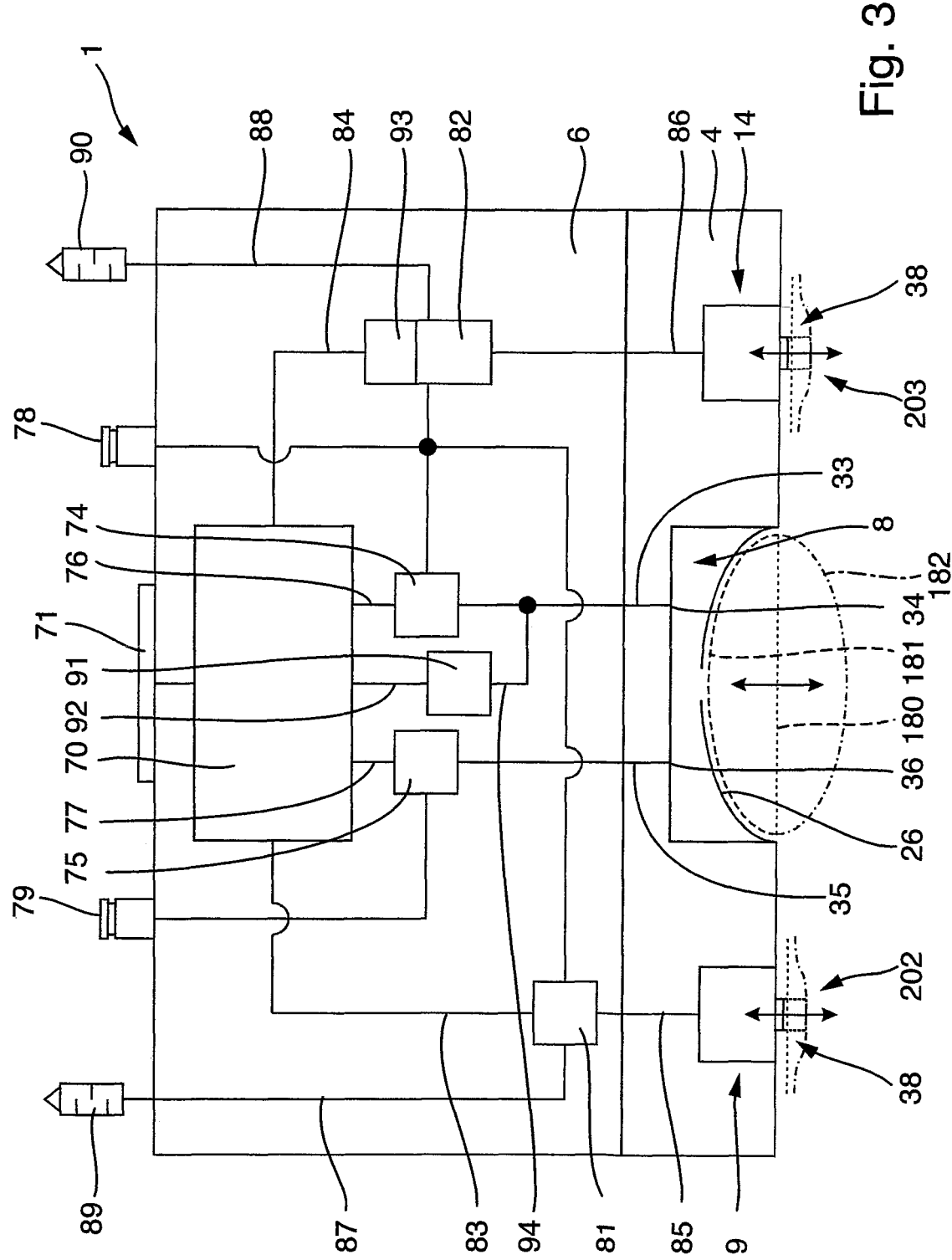
Figure 4:
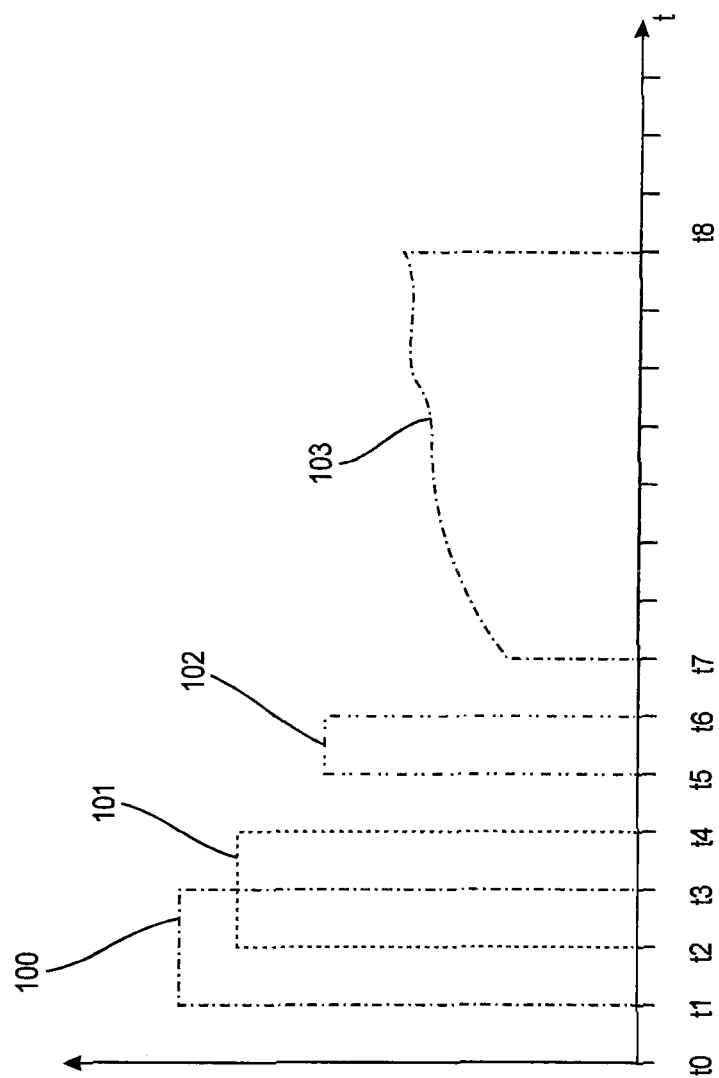

In the figures:

FIG. 1 is a sectional view of a portion of an actuating device having a control chamber and an adjustment device, FIG. 2 is a sectional view of a membrane pump device, FIG. 3 is a schematic circuit diagram of the actuating device according to FIG. 1, FIG. 4 is a control diagram for the actuating device according to FIG. 1.

The actuating device 1 shown in FIG. 1 is provided for mechanically controlling a membrane pump device 2 shown in FIG. 2, a mechanical assembly (not shown) of the actuating device 1 and the membrane pump device 2 allowing a preferably liquid fluid to be conveyed while the fluid to be conveyed is separated completely from the actuating device 1.

According to the drawing of FIG. 1, the actuating device 1, purely by way of example, is mirror-symmetrical with respect to a plane of symmetry which is oriented perpendicularly to the plane of the drawing of FIG. 1 and comprises a central axis 3. The actuating device 1 comprises a base body 4, which by way of example is of quadrangular form and in particular can be produced in the form of an injection moulded plastics part. Attached to an upper side 5, which by way of example is flat, of the base body 4 is a control module 6, which is described in greater detail below in connection with FIG. 3. An underside of the base body 4, which by way of example is at least substantially flat, serves as a mounting face 7 for the membrane pump device 2 which is shown in FIG. 2 and is likewise described in greater detail below.

As is apparent from the partially cutaway drawing in FIG. 1, a control chamber 8 and an adjustment device 9 are arranged in the base body 4. The control chamber 8 is provided for actuating a membrane 201 of a membrane pump 200, which is formed in the membrane pump device 2. The adjustment device 9 serves to control a membrane valve 202, 203, which is likewise formed in the membrane pump device 2.

The control chamber 8 is, by way of example, in the form of a rotationally symmetrical recess in the mounting face 7, the central axis 3 being provided as the axis of rotation for a profile of the control chamber 8. The control chamber 8 is substantially provided with a cup-shaped cross section and has a circular bottom region 10, a tapered wall region 11, an annular contact face 12 and, adjacent thereto, a tapered discharge region 15. The bottom region 10 is formed, by way of example, by a surface of an annular sealing element 16 which is inserted in a recess 17 adjacent to the control chamber 8 and which, relative to the central axis 3, has an L-shaped profile. The sealing element 16 rests flat with a circular-cylindrical outer surface 18 on an opposite inner surface (not provided with a reference numeral) of the recess 17 and has on a shorter L-limb a radially inwardly facing annular collar 19 which is provided for sealing contact on an outer surface of a channel portion 20 which is formed rotationally symmetrically with respect to the central axis 3. In order to ensure that the sealing element 16 and the channel portion 20 are precisely positioned, the recess 17 has a radially inwardly projecting annular collar 21 on which there rests in an interlocking manner an axial, annular end face 22 of the sealing element 16. The channel portion 20 in turn rests with a step 23 on the end face 22. A central recess 24, 25 passes through each of the sealing element 16 and the channel portion 20, which central recesses are to be regarded as part of a control fluid line 33.

In the control chamber 8 a moulded body 26 is accommodated which, purely by way of example, is rotationally symmetrical with respect to the central axis 3 and comprises a main body 27, which is substantially in the form of a ball socket portion, an annular collar 28 which protrudes radially outwardly therefrom, and a support ring 29 oriented coaxially with the central axis 3. The main body 27 has a centrally arranged recess 30 passing therethrough and forms on a surface remote from the support ring 29 a contact face 31 in the shape of a spherical cap.

The annular collar 28 rests on the contact face 12 of the control chamber 8, while the support ring 29 is supported at the front end on the bottom region 10 of the control chamber 8. The contact face 31 serves to delimit a space which is referred to as the membrane working region 32 and, when the membrane pump device 2 is attached to the actuating device 1, limits deformation of the membrane 201 of the membrane pump 200. The recess 30 in the shaped body 26 serves as a control fluid opening 34.

The adjustment device 9, which by way of example is a fluidically operable linear actuator, is arranged in the base body 4 adjacent to the control chamber 8. By way of example, the adjustment device 9 comprises an adjustment member 38 which is received in a linearly movable manner in a recess 37 and which is provided for actuating the membrane valve 202, 203 of the membrane pump device 2. The adjustment member 38 is displaced into a rest position (not shown), by way of example, without the provision of pressurised fluid by the action of a spring (not shown). According to the drawing in FIG. 1, the adjustment member 38 is located in a functional position by the provision of pressurised fluid. The adjustment member 38 comprises a cylindrical plunger 39, the longitudinal axis 40 of which is oriented transversely to the mounting face 7. The plunger 39 is attached by a rear end region to a connecting plate 41 and is fixed by a front end region 42 to a sealing membrane 43 in plate form. The connecting plate 41 is, purely by way of example, in the form of a circular disc and has on a front side 44, to which the plunger 39 is attached centrally, in a radially outer region an annular support ring 45 which protrudes in the same direction as the plunger 39. As is apparent from the drawing in FIG. 1, the support ring 45 has a U-shaped cross section having a centrally arranged, peripheral groove 46 and rests on a sealing ring 48 with a convex curved support face 47 remote from the front side 44.

The sealing ring 48 is coaxial with the plunger 39 and rotationally symmetrical with respect to the longitudinal axis 40 and has a radially inner and a radially outer annular sealing bead 49, 50. The inner sealing bead 49 is accommodated in a groove-like peripheral indentation 51 in the base body 4 and is fixed to the base body 4, purely by way of example, by a threaded ring 52 which is screwed onto a screw fitting 54 of the base body 4 which is formed coaxially with the longitudinal axis 40 and is provided with a recess 53 for the plunger 39. In the same manner, the outer sealing bead 50 is likewise fixed to the base body 4 by a threaded ring 55 which is screwed with an external thread 56 into an internal thread 57 formed on the base body 4.

In a region between the inner sealing bead 49 and the outer sealing bead 50, an annular recess 60 is formed in the base body 4 opposite the support ring 45, which annular recess allows a linear movement of the adjustment member 38 along the longitudinal axis 40 and downwards according to the drawing in FIG. 1. The sealing ring 48 fixed in a sealing manner to the base body 4 determines, together with the annular recess 60, a working chamber which represents an end region of a working fluid channel 58 and can be supplied with pressurised fluid. When the working chamber is supplied in this way, the adjustment member is displaced from a rest position (not shown) into the functional position according to FIG. 1 on account of elastic deformation of the sealing ring 48. The sealing membrane 43 is thereby also deformed and can be brought from a position protruding from the mounting face 7 into the position according to FIG. 1 which is at least substantially flush with the surface. It is provided for the sealing membrane 43 to rest in the rest position on the associated membrane valve 202, 203 of the membrane pump device 2, in order to bring the membrane valve 202, 203 from an open position into a closed position. When pressurised fluid is applied to the working chamber, the associated displacement of the adjustment member 38 into the functional position according to FIG. 1 effects an opening movement 30 for the associated membrane valve 202, 203 of the membrane pump device 2, as is shown schematically also in FIG. 3.

The sealing membrane 43 has on an upper side 61 facing the plunger 39 an annular collar 62 which is provided with a radially inwardly facing projection 63 which engages in an interlocking manner into an annular groove 64 formed on the front end region 42. This interlocking connection between the plunger 39 and the sealing membrane 43 allows a bidirectional force transmission from the plunger 39 to the sealing membrane 43 and vice versa. In a radially outer peripheral region of the sealing membrane 43, the sealing membrane is provided with a coaxially protruding, integrally formed holding ring 65 which is fixed by frictional engagement in an annular groove 66 formed in the manner of a groove in the base body 4 coaxially with the longitudinal axis 40, so that the sealing membrane 43 ensures fluidic separation between the movement chamber 59 and the environment around the actuating device.

FIG. 2 is a purely schematic sectional view of a membrane pump device 2 which is designed to be coupled to the actuating device 1 and can be used to convey a fluid, which is provided at an input port 204, to an output port 205. By way of example, the membrane pump device 2 comprises a quadrangular base plate 206, which is provided on an underside 207 with a recess 208. The recess 208 is at least largely filled with a closure plate 210 which is mounted from the underside 207 and has in a central region remote from the underside 207 a support projection 211 which extends towards the upper side 209 and has on an end face 212 remote from the underside 207 a concave, in particular spherical cap shape. A pump chamber 252 is thereby formed in a pump chamber body 253, which is part of the housing body 254 of the pump device 2. The recess 208 in the base plate 206 is formed such that, after mounting the closure plate 210 in the base plate 206, a groove-shaped inflow channel 213 and a groove-shaped outflow channel 214 are formed, each of which opens towards the upper side 209 at openings 215, 216 adjacent to the support projection 211. At an end region remote from the support projection 211, the inflow channel 213 opens into a valve chamber 217, which by way of example is cylindrical, of a first membrane valve 202; in the same manner, the outflow channel 214 opens at an end region remote from the support projection 211 into a valve chamber 218, which by way of example is cylindrical, of a second membrane valve 203.

The first membrane valve 202 is provided as an inlet valve for influencing an inflow path 219, which includes the input port 204, the valve chamber 217 and the inflow channel 213. For this purpose, an annular valve seat 220 is arranged in the valve chamber 217, the end face 221 of which annular valve seat is spaced apart from the upper side 209 of the base plate 206 and through the centre of which annular valve seat a valve channel 222 passes. By contrast, the fluidic connection between the valve chamber 217 and the inflow channel 213 is realised in a radially outer region of the valve chamber 217.

The second membrane valve 203 is provided as an outlet valve for influencing an outflow path 223, which includes the output port 205, the valve chamber 218 and the outflow channel 214. For this purpose, an annular valve seat 224 is arranged in the valve chamber 218, through the centre of which annular valve seat a valve channel 240 passes. The end face of the valve seat 224 is spaced apart from the upper side 209 of the base plate 206. The valve seat 224 is surrounded concentrically by the valve chamber, the outflow channel 214 connecting the opening 216 of the membrane pump 200, that is to say the outlet opening thereof, to the valve chamber 218. The fluidic connection between the valve chamber 218 and the output port 205 is realised in a radially outer region of the valve chamber 218. The outflow path 223 includes, in addition to the first outflow channel 214 leading to the outlet valve 203, a second outflow channel 214A which branches off from the outlet valve 203 and is connected to the valve channel 240. The second outflow channel 214A connects the valve channel 240 to the output port 205.

When the outflow path includes a first outflow channel which connects the outlet opening of the pump chamber to an inlet opening of the valve chamber of the outlet valve, and includes a second outflow channel which connects the outlet valve channel to the output port, the cross-sectional area of the outlet valve seat being smaller than the cross-sectional area of the region of the outlet valve chamber surrounding the outlet valve seat, the behaviour of regulation of the liquid flow can be improved further. It has been shown that regulation in such an arrangement is not susceptible to vibrations. However, it is also possible in principle for the first outflow channel to connect the outlet opening of the pump chamber to the outlet valve channel and for the second outflow channel to connect an outlet opening of the valve chamber of the outlet valve to the output port.

Purely by way of example, the entire upper side 209 of the base plate 206 is coated with a rubber-elastic membrane 201 which is fixed to the upper side 209 by being integrally bonded, for example, and thus ensures fluidic separation between the valve chambers 217, 218 and an environment around the membrane pump device 2. Furthermore, the membrane 201 also serves to separate a pump chamber 227, which is delimited by the recess 208 and by the support projection 211 and the membrane 201, from the environment around the membrane pump device 2.

When the membrane pump device 2 is attached to the actuating device 1, it is possible by means of the first adjustment device 9 shown in FIG. 1 to effect deformation of the membrane 201 over the valve seat 220, for example, in order thereby to press the membrane 201 onto the end face 221 of the valve seat 220 in a locally sealing manner and thus interrupt a fluidic connection between the input port 204 and the inflow channel 213. Furthermore, by means of a second adjustment device 9 (14), which is the mirror-image of that shown in FIG. 1 and which is not shown in FIG. 1 for reasons of clarity, deformation of the membrane 201 over the valve seat 224 can be effected, in order thereby to press the membrane 201 onto the end face 225 of the valve seat 224 in a locally sealing manner and thus interrupt a fluidic connection between the first outflow channel 214 and the output port 205.

In addition, the membrane 201 in the region of the pump chamber 227 above the support projection 211 can be brought, by suitably applying control fluid or a vacuum to the recess 30, from the neutral position shown in FIG. 2 into a convex suction configuration shown purely schematically in FIG. 3 or into a concave discharge configuration shown purely schematically in FIG. 3.

As has already been stated above, the actuating device 1 shown in FIG. 3 is divided, purely by way of example, into the base body 4 and the control module 6, the components contained in the base body 4 having already been described in detail above in connection with FIG. 1.

The control module 6 contains a control device 70 which can be in the form of a microprocessor or microcontroller, for example, and which is designed to execute a predefinable sequence program. By way of example, it is provided for the control device 70 to be brought via an interface 71 into electrical connection with a higher-order control device (not shown), which can be, for example, a programmable logic controller, so that the higher-order control device is able to give control commands to the control device 70. Alternatively, it is provided for the control device 70 to be able to function independently without external commands and to suitably control the components described in greater detail below. Those components are on the one hand a control fluid arrangement 72 for supplying control fluid to the control chamber 8, and on the other hand a working fluid arrangement 73 for supplying working fluid to the two adjustment devices 9, 14 shown schematically, which can be referred to as the inlet adjustment device 9 and the outlet adjustment device 14.

The control fluid arrangement 72 comprises a first control fluid valve 74 and a second control fluid valve 75, which can each, by way of example, be in the form of solenoid valves and which are electrically connected to the control device 70 via control lines 76, 77. The first control fluid valve 74 is fluidically connected via the first control fluid line 33, which opens in the control chamber 8 having a first control fluid opening 34. Furthermore, the first control fluid valve 74 is fluidically connected to a first control fluid port 78 and allows a fluidic connection between the first control fluid port 78 and the first control fluid opening 34 to be either released or blocked.

The second control fluid valve 75 is fluidically connected via a second control fluid line 35, which opens in the control chamber 8 having a second control fluid opening 36. Furthermore, the second control fluid valve 75 is fluidically connected to a second control fluid port 79 and allows a fluidic connection between the second control fluid port 79 and the second control fluid opening 36 to be either released or blocked.

It is preferably provided for a compressed air source (not shown) to be connected to the first control fluid port 78, while a vacuum source (not shown) is connected to the second control fluid port 79. When the membrane pump device 2 shown in FIG. 2 is attached to the actuating device 1 shown in FIG. 3, it is accordingly possible, by controlling the two fluid control valves 74 and 75 in a suitable, preferably alternating, in particular cyclically recurring manner, to execute a sequence of pressurising and applying a vacuum to the control chamber 8, so that the membrane 201 of the membrane pump 200 can be brought from the neutral position 180 first into a convex curved suction position 181 and then into a concave curved discharge position 182. This alternating deformation of the membrane 201 of the membrane pump 200 effects a conveying stroke for a fluid accommodated in the membrane pump 200 so that, with suitable control of the membrane valves 202 and 203, the fluid can be conveyed from the input port 204 to the output port 200. In order to be able to effect this control of the two membrane valves 202 and 203, the inlet and outlet adjustment devices 9 and 14 are provided, each of which is able to act together with the associated inlet and outlet adjustment members 38 on the opposite portions of the membrane 201 in order either to allow the membrane 201 to rest in a sealing manner on the respective valve seat 220, 224 or to allow the respective valve seat 220, 224 to be released.

For this purpose, the inlet adjustment device 9, which purely by way of example is provided for influencing the membrane valve 202 associated with the inflow channel 213, comprises a first working fluid valve 81 which is connected via a control line 83 to the control device 70 in order to allow the working fluid valve 81 to be controlled electrically. Furthermore, the working fluid valve 81 is fluidically connected to the first control fluid port 78 and is fluidically coupled to the first adjustment device 9 via a first working fluid line 85. Accordingly, the working fluid valve 81, which can be in particular a 2/2-way solenoid valve, can effect either the supply of pressurised working fluid to the inlet adjustment device 9 or the removal of air from the adjustment device 9, the removal of air taking place via a first air removal channel 87 to a first sound absorber 89. As is apparent from the drawing in FIG. 1, applying pressurised fluid to the first adjustment device 9 leads to an adjustment movement of the plunger 39, so that the sealing membrane 43, which is in a neutral position in FIG. 1, is deflected downwards and the membrane 201 of the membrane pump device 2 which can be attached therebeneath can be pressed onto the valve seat 220 in order thereby to generate the desired blocking action for the inflow channel 213.

The outlet adjustment device 14, which purely by way of example is provided for influencing the membrane valve 203 associated with the outflow channel 214, comprises a second working fluid valve 82 which is connected via a control line 84 to the control device 70 in order to allow the working fluid valve 82 to be controlled electrically. Furthermore, the working fluid valve 82 is fluidically connected to the first control fluid port 78 and is fluidically coupled to the outlet adjustment device 14 via a second working fluid line 86. Accordingly, the working fluid valve 82, which can be in particular a 3/3-way piezo pressure regulating valve, can effect either the supply of pressurised working fluid to the second adjustment device 14 or the removal of air from the second adjustment device 14, the removal of air taking place via a second air removal channel 88 to a second sound absorber 90.

As is apparent from the drawing in FIG. 1, applying pressurised fluid to the outlet adjustment device 14 leads to an adjustment movement of the plunger 39, so that the downwardly deflected sealing membrane 43 in a neutral position in FIG. 1, which presses the membrane 201 of the membrane pump device 2 which can be attached therebeneath onto the valve seat 224 so that a blocking action for the outflow channel 214 is generated, can be brought into a functional position in which the sealing membrane 43 is at least approximately flat, as is shown in FIG. 1 and whereby the membrane 201 of the membrane pump device 2 which can be attached therebeneath is lifted from the valve seat 224 on account of its resilient properties and releases the outflow channel 214.

For pressure regulation in the control chamber 8 a pressure sensor 91 is provided which is electrically connected to the control device 70 via a sensor line 92 and which, purely by way of example, is fluidically connected to the first control fluid line 33 by means of a fluid line 94. The pressure sensor 91 is thereby able to determine the fluid pressure present in the control chamber 8 and transmit it as an electrical signal to the control device 70 via the sensor line 92.

By way of example, a pressure sensor 93 is additionally associated with the second working fluid valve 82, and, purely by way of example, is integrated into the second working fluid valve 82 and is electrically connected to the control device 70 via the associated second control line 84.

FIG. 4 shows a strictly schematic, exemplary sequence for the control signals 101 to 104, which are provided by the control device 70 for controlling the individual components of the actuating device 1. Neither the signal levels nor the time segments are chosen to scale.

At a time t0, no control signal is transmitted by the control device 70. Accordingly, the two adjustment devices 9, 14 are each in a rest position in which the associated adjustment member 38 allows the respective sealing membrane 43 to protrude from the mounting face 7 and deformation of the membrane of the respective opposite membrane valves 202, 203 is accordingly ensured. This is apparent from FIG. 3 on the basis of the membrane, indicated by dot-and-dash lines, of the membrane valves 202, 203. Accordingly, both the inflow channel 213 and the outflow channel 214 are blocked at this time.

At a time t1, the control device 70 transmits a control signal 100 for the first working fluid valve 81, so that the working fluid valve is switched from an air removal position into an air admission position and pressurisation of the inlet adjustment device 9 takes place. As a result of this pressurisation, the plunger 39 of the inlet adjustment device 9 moves from the neutral position according to FIG. 3, in which the sealing membrane 43 protrudes from the mounting face 7 and the membrane, shown in FIG. 3 by a dot-and-dash line, of the associated membrane valve 202 is deformed, into a functional position, as is shown by a broken line in FIG. 3. The membrane valve 202 of the membrane pump device 2 which can be attached opposite is thereby opened, as is shown by a broken line in FIG. 3, and at least in principle allows an inflow of fluid from the input port 204 into the membrane pump 200.

At a time t2, the control circuit 70 transmits a control signal 101 to the second control fluid valve 75, so that the control fluid valve is switched from a blocking position into a release position and a vacuum is applied to the control chamber 8. As a result of this application of vacuum, the membrane 201 of the membrane pump 200 is drawn into the control chamber 8 and rests on the contact face 31 of the moulded body 26, so that it assumes the convex curved suction position 181. At this time, the pump chamber 227 of the membrane pump 200 has a maximum volume, the fluid to be conveyed being drawn from the input port 204 into the pump chamber 227 as the membrane 201 is deformed.

At a time t3, the control circuit 70 switches off the control signal 100 for the first working fluid valve 81, so that the working fluid valve is switched from the air admission position into the air removal position and pressurisation of the inlet adjustment device 9 is terminated. As a result, the plunger 39 of the inlet adjustment device 9 moves, in particular owing to a spring action of a return spring (not shown), from the functional position shown in FIG. 1 into a neutral position protruding from the mounting face 7, as is shown by a dot-and-dash line in FIG. 3, so that the membrane valve 202 of the membrane pump device 2 which can be attached opposite is closed. At this time t3, the inflow channel 213 in the membrane pump device 2 is blocked and fluid is prevented from escaping from the pump chamber 227 of the membrane pump 200.

At a time t4, the control signal 101 is switched off by the control circuit 70, so that the second control fluid valve 76 again assumes the blocking position and the control chamber 8 first has a constant vacuum starting from this time t4.

At a time t5, the control circuit 70 transmits a control signal 102 to the first control fluid valve 74, so that the first control fluid valve is switched from a blocking position into a release position and pressurisation of the control chamber 8 takes place. As a result of this pressurisation, the fluid accommodated in the membrane pump 200 is additionally placed under pressure. The pressure in the control chamber 8 is preferably such that, in a subsequent discharge operation, the membrane 201 of the membrane pump 200 is deformed completely from the convex curved suction position 181 into the concave curved discharge position, so that a maximum amount of fluid can be conveyed by means of the membrane pump 200.

At a time t6, the control signal 102 is switched off by the control circuit 70 so that the first control fluid valve 74 again assumes the blocking position.

At a time t7, the control circuit 70 provides a control signal 103 for the second working fluid valve 82 so that the second working fluid valve is able to perform a regulated adjustment movement of the plunger 39 associated with the outlet adjustment device 14. The control signal 103 is calculated in the control circuit 70 by means of an observer algorithm depending on pressure signals of the pressure sensor 91 in order, for example, to effect as constant as possible a mass flow rate of fluid from the membrane pump 200 to the output port 205.

Accordingly, the position of the plunger 39 changes dynamically during the fluid conveying operation, the membrane valve 203 being operated in the manner of a proportional valve. Owing to the excess pressure in the control chamber 8, the fluid in the pump chamber 227 of the membrane pump 200 is displaced to the output port 205, and this operation preferably continues until the membrane 201 rests flat on the end face 212 of the support projection 211 and the pump chamber 227 is thus at least approximately completely empty.

At a time t8, the control circuit 70 switches off the control signal 103, so that at this time the conveying operation for the membrane pump 200 is terminated and a new conveying operation can begin.

The invention claimed is:

1. An actuating device for mechanically controlling a membrane pump device for conveying fluids, the actuating device comprising a base body that comprises a mounting face for mounting a membrane pump device and through which a control fluid line passes, the control fluid line extending from a control fluid port to a control fluid opening that opens at the mounting face, a control fluid valve arranged in the control fluid line and designed to influence a cross section of the control fluid line, an adjustment device that comprises a fluid actuator arranged on the mounting face for providing an adjustment movement, and a working fluid valve that is designed to influence a cross section of a working fluid line that passes through the base body, wherein the working fluid valve is fluidically coupled to the adjustment device via the working fluid line, a working fluid pressure sensor is arranged in the working fluid line and is configured to detect a working fluid pressure in the working fluid line, the control fluid valve, the working fluid valve, and the working fluid pressure sensor are electrically connected to a control device that is designed to electrically control the control fluid valve and the working fluid valve, a control fluid pressure sensor is arranged on the base body, and the control fluid pressure sensor is electrically connected to the control device and is designed to detect a control fluid pressure.

2. The actuating device according to claim 1, wherein the control device includes an observer algorithm and is configured such that, on the basis of the observer algorithm, a mass flow rate of fluid of the membrane pump device is determined depending on pressure signals from the control fluid pressure sensor.

3. The actuating device according to claim 1, wherein a concave control chamber is formed on the mounting face as a movement chamber for a pump membrane, and the control fluid opening opens at a surface of the control chamber.

4. The actuating device according to claim 1, wherein the working fluid line is fluidically connected to the control fluid port.

5. A membrane pump for conveying fluids, comprising the actuating device and the membrane pump device according to claim 1.

6. The membrane pump according to claim 5, wherein the membrane pump device has:

a pump chamber body in which there is formed a recess that is closed by a resilient membrane to form a pump chamber, an inflow path that connects an input port to an inlet opening of the pump chamber, an outflow path that connects an outlet opening of the pump chamber to an output port, an inlet valve provided in the inflow path for influencing the flow of liquid in the inflow path, and an outlet valve provided in the outflow path for influencing the flow of liquid in the outflow path.

7. A blood treatment device having a container for providing a medical liquid, and the membrane pump according to claim 5 for conveying a medical liquid.

8. The blood treatment device of claim 7, wherein said blood treatment device is a dialysis device.

9. The blood treatment device of claim 7, wherein said medical liquid is an anticoagulation solution.

10. The membrane pump of claim 5, wherein said conveying fluids are medical liquids for blood treatment.

11. The actuating device of claim 1, wherein said conveying fluids are medical liquids for blood treatment.

12. An actuating device for mechanically controlling a membrane pump device for conveying fluids, the actuating device comprising a base body that comprises a mounting face for mounting a membrane pump device and through which a control fluid line passes, the control fluid line extending from a control fluid port to a control fluid opening that opens at the mounting face, a control fluid valve arranged in the control fluid line and designed to influence a cross section of the control fluid line, an adjustment device that comprises a fluid actuator arranged on the mounting face for providing an adjustment movement, and a working fluid valve that is designed to influence a cross section of a working fluid line that passes through the base body, wherein the control fluid valve and the working fluid valve are electrically connected to a control device that is designed to electrically control the control fluid valve and the working fluid valve,
a vacuum line is formed in the base body,
the vacuum line extends from a vacuum port to a control chamber or to the control fluid line,
a vacuum valve is arranged in the control fluid line and is designed to influence a cross section of the vacuum line,
the vacuum valve is electrically connected to the control device,
a control fluid pressure sensor is arranged on the base body, and
the control fluid pressure sensor is electrically connected to the control device and is designed to detect a control fluid pressure.

13. An actuating device for mechanically controlling a membrane pump device for conveying fluids, the actuating device comprising a base body that comprises a mounting face for mounting a membrane pump device and through which a control fluid line passes, the control fluid line extending from a control fluid port to a control fluid opening that opens at the mounting face, a control fluid valve arranged in the control fluid line and designed to influence a cross section of the control fluid line, a first adjustment device and a second adjustment device each arranged on the base body and each comprising a respective fluid actuator arranged on the mounting face for providing an adjustment movement, the first adjustment device having a first working fluid valve and the second adjustment device having a second working fluid valve, the first working fluid valve and the second working fluid valve are each designed to influence a cross section of at least one working fluid line that passes through the base body, wherein the control fluid valve, the first working fluid valve, and the second working fluid valve are electrically connected to a control device that is designed to electrically control the control fluid valve, the first working fluid valve, and the second working fluid valve, the first working fluid valve is in the form of a switch valve and the second working fluid valve is in the form of a proportional valve.

14. The actuating device according to claim 13, wherein the control device is configured such that the second working fluid valve is controlled by the control device, the control device determines a mass flow rate of fluid in the membrane pump device, and the control device determines a target pressure value for the second working fluid valve, depending on the determined mass flow rate of fluid, in such a manner that a constant mass flow rate of fluid is generated during a discharge phase of the membrane pump device.

15. The actuating device of claim 13, wherein the second working fluid valve is in the form of a pressure regulating valve.

16. A method for operating an actuating device for mechanically controlling a membrane pump device, the actuating device comprising a base body that comprises a mounting face for mounting a membrane pump device and through which a control fluid line passes, the control fluid line extending from a control fluid port to a control fluid opening that opens at the mounting face, a control fluid valve arranged in the control fluid line and designed to influence a cross section of the control fluid line, an adjustment device that comprises a fluid actuator arranged on the mounting face for providing an adjustment movement, and a working fluid valve that is designed to influence a cross section of a working fluid line that passes through the base body, wherein the control fluid valve and the working fluid valve are electrically connected to a control device that is designed to electrically control the control fluid valve and the working fluid valve, wherein on the basis of an observer algorithm, the control device determines a mass flow rate of fluid in the membrane pump device depending on pressure signals of a control fluid pressure sensor, and the control device determines a target pressure value for the working fluid valve depending on the determined mass flow rate of fluid, in order to ensure a constant mass flow rate of fluid during a discharge phase of the membrane pump device.

17. The method according to claim 16, wherein the actuating device further comprises a vacuum line and a vacuum valve, and the control device controls the control fluid valve and the vacuum valve during a discharge phase of the membrane pump device in such a manner that the control fluid line and the vacuum line are blocked.

* * * * *